United States Patent [19]

Aggarwal et al.

[11] 4,260,519

[45] Apr. 7, 1981

[54] PREPARATION OF BARIUM-ALKOXIDE SALTS

[75] Inventors: Sundar L. Aggarwal, Akron; Ivan G. Hargis, Tallmadge; Russell A. Livigni; Hubert J. Fabris, both of Akron, all of Ohio

[73] Assignee: The General Tire & Rubber Company, Akron, Ohio

[21] Appl. No.: 142,790

[22] Filed: Apr. 22, 1980

Related U.S. Application Data

[62] Division of Ser. No. 77,428, Sep. 20, 1979.

[51] Int. Cl.$^3$ ............................................. C08F 4/48
[52] U.S. Cl. ............................. 252/431 L; 526/173; 526/181
[58] Field of Search ..................... 526/181; 252/431 L

[56] References Cited

U.S. PATENT DOCUMENTS

| 3,629,213 | 12/1971 | Onishi et al. | 252/431 C X |
|---|---|---|---|
| 3,846,385 | 11/1974 | Hargis et al. | 252/431 R X |
| 3,992,561 | 11/1976 | Hargis et al. | 526/181 |
| 4,020,115 | 4/1977 | Hargis et al. | 568/851 |
| 4,033,900 | 7/1977 | Hargis et al. | 252/431 L |

OTHER PUBLICATIONS

Fujio et al., "Copolymerization of Butadiene & Styrene", J. Chem. Soc., Japan, (1972), pp. 447-453.

*Primary Examiner*—Patrick Garvin

[57] ABSTRACT

The characteristics of barium t-alkoxide salts used with organolithium compounds as catalyst complexes in the solution polymerization of unsaturated or oxirane monomers to make polymers such as rubbers is improved by reducing or eliminating the nitrogen content of the barium salt and, further, by using a certain mixture of tertiary carbinols and water in forming the barium salt. In certain instances water may be eliminated.

6 Claims, No Drawings

PREPARATION OF BARIUM-ALKOXIDE SALTS

This is a division of application Ser. No. 077,428 filed Sept. 20, 1979.

This invention relates to the preparation of barium t-alkoxide salts useful as catalysts with organolithium compounds for the solution polymerization of ethylenically unsaturated monomers like butadiene and heterocyclic monomers such as oxirane monomers like propylene oxide. Other heterocyclic monomer classes such as siloxanes, thiiranes, thiatanes and lactams can also be polymerized using the catalyst of this invention.

BACKGROUND OF THE INVENTION

A catalyst system for diene polymerization using an organolithium compound in combination with a barium compound including barium stearate and barium t-butoxide, without showing how the barium compounds are made, is stated to provide random copolymers of certain dienes and mono-vinyl aromatic compounds, having a vinyl content of 7.8–13% and a trans content using Ba t-butoxide as high as 67.9% and using barium stearate as high as 70.5% (Examples 1 and 13, U.S. Pat. No. 3,629,213 (1971), Akira Onishi, Ryota Fujio, Minoru Kojima and Hiroshi Kawamoto, assignors to Bridgestone Tire Company Limited). Ryota Fujio, Minoru Kojima, Shiro Anzai and Akira Onishi (Bridgestone Tire Co., Ltd.), "Kogyo Kagaku Zasshi," No. 2 (1972), pages 447-453, in a somewhat similar disclosure show the reaction product of alkaline earth metals directly with active hydrogen containing compounds (apparently in benzene) and their use with organolithiums as catalysts. The use of barium stearate with an organolithium was said to provide 5.25%–59% trans for a butadiene-styrene copolymer. It was stated that barium stearate is scarcely effective and showed a maximum of 67.9% trans for SBR using barium t-butoxide and an organolithium.

U.S. Pat. No. 3,992,561 (I. G. Hargis, R. A. Livigni and S. L. Aggarwal; divisional U.S. Patents of the same Nos. 4,020,115; 4,033,900 and 4,048,427 have the same disclosure) discloses that barium t-alkoxide hydroxide salts in conjunction with organolithium compounds provide catalyst complexes useful in the solution polymerization of various vinyl or ethylenically unsaturated monomers. In particular, this patent discloses the preparation of polymers of butadiene and copolymers of butadiene and styrene having high trans contents (up to 80.4%) for the butadiene placements or segments. These polymers, also, exhibit a high viscosity and other desirable properties such as green strength and tack strength.

An object of this invention is to provide an improved barium t-alkoxide salt useful with organo-lithium compounds to form anionic catalyst complexes for polymerizing ethylenically unsaturated monomers and heterocyclic monomers.

Another object of this invention is to provide a method for making an improved barium t-alkoxide salt which is useful in conjunction with an organolithium compound to form anionic catalyst complexes which can cause polymerization of unsaturated monomers in solvent polymerization systems.

A further object of this invention is to provide a method for polymerizing unsaturated monomers or heterocyclic monomers using an anionic catalyst complex of an organo-lithium compound and a barium t-alkoxide salt.

These and other objects and advantages of the present invention will become more apparent to those skilled in the art from the following detailed description and working examples.

SUMMARY OF THE INVENTION

It has been found that treatment of the barium t-alkoxide-hydroxide salt or mixed barium t-alkoxide salts under vacuum at a temperature and for a time sufficient to reduce the amount of nitrogen so that the nitrogen content is not greater than about 0.1%, preferably not greater than about 0.01%, by weight (Kjeldahl method), thus being virtually $N_2$ free, gives higher rates of polymerization for butadiene and more reproducible polymer microstructure. U.S. Pat. No. 3,992,561, above, discloses that the barium salts are prepared in liquid $NH_3$ or amine solvent from the reaction of barium with a mixture of t-butanol and water and recovered from the amine compound by vacuum drying at 50° C. to contain 0.5 wt% nitrogen (column 6, lines 53–61 and column 12, lines 29–35). Gas Chromatography/Mass Spectroscopy (GS/MS) analysis has shown that amine is also present in toluene solutions of the barium salts.

It, also, has been found that if the tertiary carbinol used in making the barium salt is partly replaced by another different tertiary carbinol or by mixtures of different tertiary carbinols and the same treatment is followed, a salt is obtained which is more soluble. Furthermore, the solution of the barium salt is more stable on aging. Catalysts prepared using barium salts with low nitrogen content provide polymers with a higher viscosity (higher molecular weight).

Moreover, it further has been found that if mixtures of different t-carbinols as described below are used for reaction with the barium metal to make the barium salt, it is not necessary to add water to the reaction mixture of the t-carbinols and barium in ammonia or amine solvent. The resulting barium alkoxide salts then treated as above when used with organolithium compounds, provide complexes which can be used to polymerize butadiene to a high trans content.

The reduction in nitrogen (amine) concentration in either the barium t-alkoxide(s)-hydroxide salt or the barium mixed t-alkoxide(s) salt does not greatly alter the amount of trans-1,4 content of the butadiene segments of the polymers obtained. Moreover, the previously shown relationships as described in the above U.S. Pat. No. 3,992,561 between polymer structure and polymerization variables are not significantly affected except for the variation in trans-1,4 content with the $Ba^{2+}/Li^+$ mole ratio, which has been changed somewhat, and the use of cyclohexane as a polymerization solvent for the preparation of high molecular weight butadiene based polymers with 79–80% trans-1,4 content.

DISCUSSION OF DETAILS AND PREFERRED EMBODIMENTS

The barium tertiary alkoxide salt is obtained by reacting barium metal with (A) a mixture of a tertiary carbinol and water, (B) a mixture of a mixture of tertiary carbinols and water or (C) a mixture of tertiary carbinols in liquid $NH_3$ or amine solvent. This reaction is carried out at a temperature of from about −100° C. up to the boiling point of the solvent.

The basic tertiary carbinol used has the general formula

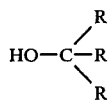

where at least one of the Rs is a methyl or cyclohexyl radical and the remaining Rs are selected from the group consisting of alkyl or cycloalkyl radicals of from 1 to 6 carbon atoms which may be the same or different such as a methyl, ethyl, propyl, isopropyl, amyl, cyclohexyl and the like radicals. Preferably in the tertiary carbinol used, the Rs are all methyl groups. Examples of these tertiary carbinols are t-butanol, 3-methyl-3-pentanol, 2-methyl-2-butanol, 2-methyl-2-pentanol, 3-methyl-3-hexanol, 3,7-dimethyl-3-octanol, 2-methyl-2-heptanol, 3-methyl-3-heptanol, 2,4-dimethyl-2-pentanol, 2,4,4-trimethyl-2-pentanol, 2-methyl-2-octanol, tricyclohexyl carbinol, dicyclopropyl methyl carbinol, dicyclohexyl propyl carbinol and cyclohexyl dimethyl carbinol and the like and mixtures thereof.

The other tertiary or second carbinol used when mixtures of t-carbinols are employed has the general formula

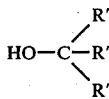

where R' is an alkyl radical of from 2 to 6 carbon atoms which may be the same or different. R', thus, can be an ethyl, propyl, isopropyl, butyl, isobutyl radical and so forth. Examples of such tertiary carbinols are t-decanol (4-n-propylheptanol-4), 3-ethyl-3-pentanol, 3-ethyl-3-hexanol, 3-ethyl-3-heptanol, 3-ethyl-3-octanol, 5-ethyl-5-nonanol, 5-ethyl-5-decanol, 6-ethyl-6-undecanol, 5-butyl-5-nonanol, 4-isopropyl-4-heptanol, 2-methyl-4-n-propyl-4-heptanol, 4-n-propyl-4-nonanol, 5-n-propyl-5-nonanol, 2,2-dimethyl-4-n-propyl-4-heptanol, 4-n-propyl-4-decanol, 5-n-propyl-5-decanol, 2,6-dimethyl-4-isobutyl-4-heptanol, 3,3,6-trimethyl-4-n-propyl-4-heptanol, 6-n-propyl-6-undecanol, 5-n-butyl-5-decanol, 6-n-butyl-6-undecanol, 6-n-pentyl-6-undecanol, 2,8-dimethyl-5-isopentyl-5-nonanol, and 2,8-dimethyl-5-isobutyl-5-nonanol and the like and mixtures of the same. Of these tertiary carbinols t-decanol is preferred.

In partial or entire replacement of the above second named t-carbinol there may be used a tertiary carbinol having the general formula

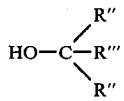

where R" is an alkyl radical of from 1 to 4 carbon atoms which may the same or different and where R''' is a hydrocarbon radical having a molecular weight of from about 250 to 5,000. These materials may be obtained by polymerizing in solvent media butadiene and/or isoprene with or without a minor amount of styrene and/or alpha methyl styrene using a monolithium hydrocarbon catalyst such as butyllithium to obtain a liquid lithium terminated polymer or oligomer. The preparation of such liquid diene containing polymers is known. See U.S. Pat. No. 3,078,254. Appreciable amounts of catalyst are used to obtain liquid polymers. See U.S. Pat. No. 3,301,840. The resulting polymer solution is then treated with an epoxide such as isobutylene oxide

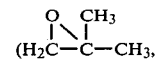

1,1-dimethyl-1,2epoxyethane or 1,2-epoxy-2-methyl propane) to obtain a product which may be shown as:

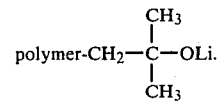

In place of isobutylene oxide there can be used 1,1-diethyl-1,2-epoxyethane, 1,1-dipropyl-1,2-epoxyethane, 1,1-diisopropyl-1,2-epoxyethane, 1,1-dibutyl-1,2-epoxyethane, 1,1-diisobutyl-1,2-epoxyethane and the like epoxide and mixture thereof. See U.S. Pat. No. 3,538,043. These epoxide treated lithium terminated polymers can then be hydrolyzed with water to form the tertiary carbinol or alcohol:

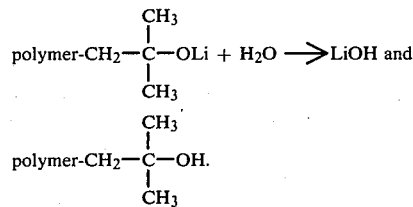

See U.S. Pat. No. 3,055,952. The hydrolyzed polymer or liquid tertiary carbinol is then removed from the organic solvent and is ready for reaction with barium to form a barium tertiary alkoxide salt.

When the mixture of tertiary carbinols is used, the mol ratio of

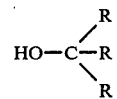

to at least one of

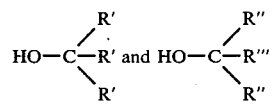

is from about 1:0.3 to 1:1. In other words, there is used about 1 mol of

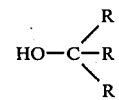

to from about 0.3 to 1 mol of

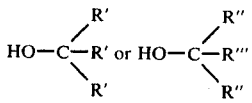

or mixture of

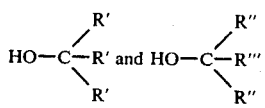

where R, R', R" and R'" are the same as defined above.

Water, when used in preparing the barium t-alkoxide salts, is employed in the t-carbinol or t-carbinol mixtures as follows:

I. from about 0.5 to 12, preferably from about 2.5 to 10, mol% of water to from about 99.5 to 88, preferably from about 97.5 to 90, mol% of

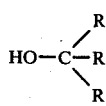

and

II. from about 0 to 12, preferably from about 0 to 10, mol% of water to from about 100 to 88, preferably from about 100 to 90, mol%

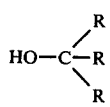

plus at least one of

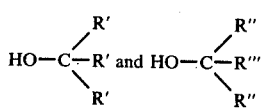

where R, R', R" and R'" are the same as defined above.

The solvent used in preparing the barium alkoxide salt is selected from the group consisting of liquid $NH_3$ and saturated, non-polymerizable, cycloaliphatic and heterocyclic, primary and secondary mono amines and poly-amines and mixtures thereof, having from 1 to 12 carbon atoms and from 1 to 3 nitrogen atoms and being a liquid at a temperature of from about $-100°$ C. up to the boiling point of the solvent and at a pressure of from about 0.25 to 10 atmospheres. Examples of such amines are methylamine, dimethylamine, ethylamine, n-propylamine, n-butylamine, n-amylamine, n-hexylamine, pentamethylene-diamine, hexamethylenediamine, di-n-propylamine, diisopropylamine, diethylamine, cyclohexylamine, N-butyl cyclohexylamine, N-ethylcyclohexylamine, N-methyl cyclohexylamine, diethylene triamine, cyclopentylamine, diamylamine, dibutylamine, diisoamylamine, diisobutylamine, dicyclohexylamine, piperidine, pyrrolidine, butyl ethylamine, and the like and mixtures thereof. Lower molecular weight amines are preferred since less is required to solvate the metal. It is preferred that the $NH_3$ or amine be pure. However, commercially available materials can be used provided that they do not contain more than about 2% by weight of by-products or impurities such as polyamines, other alcohols and water which will have to be considered when preparing the barium salt. Any material which would adversely affect the effectiveness of the barium salt as a catalyst component should be removed from the $NH_3$ or amine. The amine should be a solvent for the barium or at least dissolve it in part so that the barium can react with the tertiary carbinol(s) and $H_2O$ (if used) mixture.

In preparing the barium tertiary alkoxide salt, sufficient $NH_3$ or amine solvent is employed to dissolve the metal. Preferably, an excess of the amine or $NH_3$ is employed. When preparing the salts at low temperatures, it is not necessary to use pressure equipment. However, pressure equipment can be employed, and the process of preparing the salts can occur at pressures of from about 0.25 to 10 atmospheres depending on the vapor pressure of the amine solvent used. During preparation of the salt it is desirable to agitate the reaction mixture during addition and reaction of the reagents. Further, it is preferred that an inert atmosphere, for example, helium, neon, or argon be maintained over the reaction mixture at all times to prevent contact of the product with air. Of course, in place of the inert gas, the vapor of the organic compound and/or amine can be used as the "inert atmosphere." Closed reactors should be employed. It is not desirable to prepare the barium di-tert-alkoxide (hydroxide) salt in bulk or in mass since the reaction is slow; diluents, however, other than amines may be used.

After prepration of the barium salt, any diluent, the amine or $NH_3$ is separated by distillation, vacuum evaporation, solvent extraction and so forth utilizing temperatures, pressures and solvents which do not adversely affect the barium salt. The amine or $NH_3$ may simply be evaporated from the salt, any excess of barium or barium salts (amides) other than the alkoxide or alkoxide hydroxide salts may be removed, and the salt, dried in vacuum, for example, of less than about 20 mm mercury pressure, at a temperature and for a time sufficient to reduce the level of amine or ammonia or $N_2$ (nitrogen) in the salt so that the $N_2$ is not greater than about 0.1%, preferably not greater than about 0.01%, by weight, generally at a temperature of at least about 70° C., preferably at a temperature of from about 70° to 125° C. The nitrogen may or may not be bound. If desired, the vacuum-heat treatment may be continued to further reduce or eliminate the nitrogen content. Times for vacuum heat treatment will vary depending on whether the salt is in the form of a cake, granules or fine particles. The salt then may be dissolved in one or more organic hydrocarbon solvents such as toluene or the like. Since the amount of barium salt solution is so small in relation to the other materials, the organic hydrocarbon solvent used for the salt does not necessarily have to be, but is preferred to be, the same as that used for the polymerization solvent. Dilute solutions of the barium salt in the organic hydrocarbon solvents are generally preferred for injection into the polymerization reactor.

The yield of the barium salt based on the weight increase of the barium can be from about 95 to 100%. The solution of the barium salt in the organic solvent may be used as prepared. However, it is usually allowed to stand overnight to allow a precipitate to settle out. About 90 to 100% by weight of the barium salt (Ba-t-alkoxide(s) optionally plus hydroxide) as an active catalyst component is in the solution phase. The solution phase can be separated from the solid phase by decantation, filtration or centrifugation. While the solid phase or precipitate is not useful as a catalyst component, it can be mixed or dispersed with solution phase and used in polymerization. It will be appreciated that barium is insoluble in benzene, barium hydroxide is insoluble in benzene and toluene and barium di(tertiary butoxide) containing some nitrogen or nitrogen-free, for example, is sparingly soluble in benzene. The salt obtained from barium, t-decanol alone and water, nitrogen free, is not useful as a catalyst component since it is only sparingly soluble in toluene. Also the barium tertiary alkoxide-hydroxide salt or mixed alkoxide, amine free, salt of this invention is not an effective catalyst by itself for the polymerization of butadiene, but in combination with the organolithium component it provides rubbery, high trans, high molecular weight butadiene polymers.

The resulting barium salts containing not over about 0.1%, preferably not over about 0.01%, by weight of nitrogen have the following general formulae:

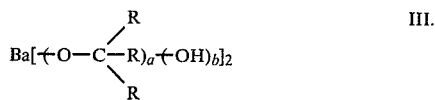
III.

where the mol ratio of a to b is from about 99.5:0.5 to 88:12, preferably from about 97.5:2.5 to 90:10, and where the Rs are as defined above and

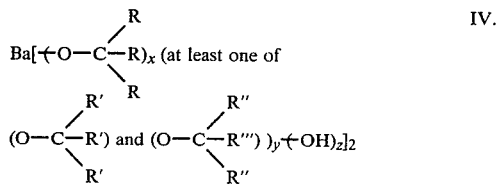
IV.

where the mol ratio of x+y to z is from about 100:0 to 88:12, preferably the mol ratio of x+y to z is from about 100:0 to 90:10, where the mol ratio of x to y is from about 1:0.3 to 1:1 and where R, R', R'' and R''' are the same as defined above.

The organolithium compound used with the barium t-alkoxide(s) (hydroxide) salt to form a catalyst complex useful in solution polymerization is an aliphatic, aromatic, aliphatic-aromatic, cycloaliphatic and so forth Li hydrocarbon compound having from 1 to 6 lithium atoms and from 2 to 200 carbon atoms. Examples of the organolithium compounds are ethyllithium, n-propyllithium, isopropyllithium, allyllithium, n-butyllithium, isobutyllithium, sec-butyllithium, tert-butyllithium, n-amyllithium, isoamyllithium, n-hexyllithium, 2-ethylhexyllithium, n-octyllithium, n-decyllithium, cyclopentyllithium, cyclohexyllithium, ethylcyclohexyllithium, cyclohexylethyllithium, phenyllithium, dilithiostilbene, 1,2-dilithio-1,2-diphenylhexane, 1,4-dilithiobutane, 1,6-dilithiohexane, dilithionaphthalene, 1,2-diphenylhexyllithium, 1,2-dilithio-1,2,3,4-tetra phenyloctane, 1,2-dilithio-1,2-diphenyl ethane, dilithiobutadiene, dilithioisoprene, dilithiopiperylene, 1,3,5-trilithiopentane, 1,5,15-trilithioeicosane, 1,3,5-trilithiocyclohexane, 1,2,5-trilithionaphthalene, 1,3,5-trilithioanthracene, 1,3,5,8-tetralithiodecane, 1,5,10,20-tetralithioeicosane, 1,2,4,6-tetralithiocyclohexane 1,2,3,5-tetralithio-4-hexylanthracene and so forth. A dilithioisoprene oligomer can, also, be used; it has the general formula

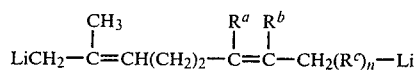

(where $R^a$=H and $R^b$=CH$_3$ or $R^a$=CH$_3$ and $R^b$=H, $R^c$=1,4 and 3,4 isoprene adducts, and n=0.2 and having an average M.W. of 162). Other oligomers can be used such as the mono and dilithium polystyryls and polybutadienyls. Other mono-and polylithiohydrocarbon compounds may be used. Mixtures of those organic lithium compounds can be used. However, it is preferred to use monolithium alkyl compounds where the alkyl radical has from 2 to 10 carbon atoms and mixtures of the same. The lithium compound should be soluble in or dispersible as microgel in the polymerization solvent.

The mol ratio of the barium salt to the organo lithium compound to form the anionic catalyst complex is from about 0.60:1 to 1.1:1 based on the metals. This ratio gives the highest trans content and average molecular weight and the highest overall polymerization rate when using butadiene. When the barium salt and organolithium are mixed in toluene, a light orange color change forms quickly indicating complex formation, whereas when benzene is used, a light red color change occurs more slowly.

Just prior to polymerization, the barium salt in hydrocarbon solution and the organo-lithium compound in hydrocarbon solution are mixed together. The time required to form a complex ranges from a few minutes to an hour or longer depending on the reaction temperature. This should be accomplished under an inert atmosphere, and the ingredients may be heated to speed reaction at temperatures of from about 25° to 100° C., preferably from about 40° to 60° C. After the complex has formed, the polymerization solvent and monomer(s) may be added to it, or the performed catalyst dissolved in its solvent may be injected into a reactor containing the monomers dissolved in the hydrocarbon polymerization solvent.

The monomers to be polymerized can be ethylenically unsaturated monomers or heterocyclic monomers. The ethylenically unsaturated polymerizable monomers to be polymerized with the catalysts of the present invention are those having an activated unsaturated double bond, for example, those monomers where adjacent to the double bond there is a group more electrophilic than hydrogen and which is not easily removed by a strong base. Examples of such monomers are nitriles like acrylonitrile and methacrylonitrile; acrylates and alkacrylates like methyl acrylate, ethyl acrylate, butyl acrylate, ethyl hexyl acrylate, octyl acrylate, methyl methacrylate, ethyl methacrylate, butyl methacrylate, methyl ethacrylate, ethyl ethacrylate, butyl ethacrylate and octyl ethacrylate; the dienes such as butaniene-1,3 and isoprene; and the vinyl benzenes like styrene, alpha methyl styrene, p-tertiary butyl styrene, divinyl benzene, methyl vinyl toluene and para vinyl toluene and the like and mixtures of the same. Examples of polymerizable heterocyclic monomers are oxiranes like ethylene oxide, propylene oxide, 1,2-butylene oxide, styrene oxide, isobutylene oxide, allyl glycidyl ether, phenyl glycidyl ether, crotyl glycidyl ether, isoprene monoxide, butadiene monoxide, vinyl cyclohexane monoxide and the like and mixtures thereof. Other heterocyclic monomers which may be polymerized are siloxanes such as octamethyl tetrasiloxane, thiiranes like propylene sulfide, thiatanes like thiacyclobutane and lactams like epsilon-caprolactam. Depending on the monomer employed, the resulting polymers can be rubbery, resinous, or thermoplastic.

Preferred monomers used in the practice of the present invention are butadiene-1,3 and mixtures of butandiene-1,3 and up to about 30% by weight total of the mixtures of styrene and/or isoprene to make rubbery homopolymers and rubbery random copolymers exhibiting a high trans-1,4 content, a low vinyl content and a high average molecular weight. Moreover, by altering the butadiene homopolymer or butadiene-copolymer composition or microstructure a rubber can be prepared which has behavior closely simulating that of natural rubber in building tack and green strength. Thus, it is within the scope of this invention to prepare polymers which can serve as replacements in those applications where natural rubber is employed such as in the tires. The obtained number-average molecular weight in the absence of chain transfer corresponds well with the molecular weight calculated from the ratio of grams of monomer polymerized to moles of carbon-lithium charged. Conversions of monomer to polymer up to about 100% may be obtained.

Temperatures during solution polymerization can vary from about $-90°$ to $100°$ C. Lower temperatures provide polymers having higher intrinsic viscosities. Preferably polymerization temperatures are from about $-20°$ to $60°$ C. and even more preferably from about $-20°$ to $30°$ C. Time for polymerization will be dependent on the temperature, amount of catalyst, type of polymers desired and so forth. Only minor amounts of catalyst complex are necessary to effect polymerization. However, the amount of catalyst employed may vary with the type of polymer desired. For example, when making polymers having a high average molecular weight using a given amount of monomer, only a small amount of the catalyst complex is necessary whereas when making a low average molecular weight polymer, larger amounts of the catalyst complex are employed. Moreover, since the polymer is a living polymer, it will continue to grow as long as monomer is fed to the polymerization system. Thus, the molecular weight can be as high as a million or even more. On the other hand, very high molecular weight polymers require lengthy polymerization times for a given amount of the catalyst complex, and at lower catalyst complex concentrations the polymerization rate drops. Moreover, high molecular weight polymers are difficult to handle in the polymerization reactor and on rubber mills and the like. A useful range of catalyst complex to obtain readily processable polymers in practicable times is from about 0.00001 to 0.10, preferably from about 0.00033 to 0.005, mole of catalyst complex computed as lithium per 100 grams total of monomer(s).

Since the polymer in solution in the polymerization media is a living polymer or since the polymerization is a non-terminating polymerization (unless positively terminated by failure to add monomer or by adding a terminating agent such as methanol), block polymers can be prepared by sequential addition of monomers or functional groups can be added. Also, since the living polymer contains a terminal metal ion, it as shown above can be treated with an epoxide like ethylene oxide and then with water to provide a polymer with a terminal hydroxyl group for reaction with a polyisocyanate to jump the polymer through formation of polyurethane linkages.

The polymerization is conducted in a liquid hydrocarbon solvent. While bulk polymerization may be used, such presents heat transfer problems which should be avoided. In solvent polymerizations it is preferred to operate on a basis of not over about 15 to 20% polymer solids concentration in the solvent to enable ready heat transfer and processing. Solvents for the monomers and polymers should not have a very labile carbon-hydrogen bond and should not act at least substantially as chain terminating agents. They preferably should be liquid at room temperature (about 25° C.). Examples of such solvents are benzene (less desirable), toluene, the xylenes, the trimethyl benzenes, hemimellitene, pseudocumene, mesitylene, prehnitene, isodurene, o, m, and p cymenes, ethylbenzene, n-propylbenzene, cumene, 1,2,4- or 1,3,5-triethylbenzene, n-butyl benzene and other lower alkyl substituted benzenes, hexane, heptane, octane, nonane, cyclohexane, cycloheptane, cyclooctane and the like and mixtures of the same. Some solvents may give lower trans contents but on the other hand may give higher molecular weights.

Polymerization, of course, should be conducted in a closed reactor, preferably a pressure reactor, fitted with a stirrer, heating and cooling means, with means to flush with or pump in an inert gas such as nitrogn, neon, argon and so forth in order to polymerize under inert or non-reactive conditions, with means to charge monomer, solvent and catalyst, venting means and with means to recover the resulting polymer and so forth.

After polymerization the catalyst may be terminated by adding water, alcohol or other agent to the polymeric solution. After the polymer has been recovered and dried, a suitable antioxidant such as 2,6-di-tert-butyl-p-cresol or other antioxidant may be added to the same. However, the antioxidant may be added to the polymeric solution before it is stripped of solvent.

The polymers produced by the method of the present invention can be compounded and cured in the same manner as other plastic and rubbery polymers. For example, they can be mixed with sulfur or sulfur furnishing materials, peroxides, carbon black, $SiO_2$, $TiO_2$, $Sb_2O_3$, red iron oxide, phthalocyanine blue or green, tetramethyl or ethyl thiuram disulfide, benzothiazyl disulfide and rubber extending or processing mineral or petroleum oils and the like. Stabilizers, antioxidants, UV light absorbers and other antidegradants can be added to these polymers. They can also be blended with other polymers like natural rubber, butyl rubber, butadiene-styrene-acrylonitrile terpolymers, polychloroprene, SBR, polyurethane elastomers and so forth.

The polymers produced by the method of the present invention can be used in making protective coatings for fabrics, body and engine amounts for automobiles, gaskets, treads and carcasses for tires, belts, hose, shoe soles, and electric wire and cable insulation, and as plasticizers and polymeric fillers for other plastics and rubbers. With large amounts of sulfur hard rubber products can be made.

The following examples will serve to illustrate the present invention with more particularity to those skilled in the art.

EXAMPLE 1

This example covers the preparation of an amine-free (not over 0.01% by weight of $N_2$) barium salt from t-decanol, t-butanol and water and differs from the preparation shown in U.S. Pat. No. 3,992,561 (Column 10, Example I) with respect to the substitution of 34 mol % of t-butanol with t-decanol and vacuum drying the barium salt at 100° C. instead of 50° C.

To 82.2 milliequivalents (meq) of barium metal (5.65 g) were added 325 ml of monomethylamine which had been flash distilled from Na-dispersion. The reactor was cooled to −78° C. with rapid stirring and a deep blue colored solution, characteristic of the amine solution of the metal, was obtained. To this solution a mixture of t-decanol (4-n-propyl-heptanol-4) (21 milliequivalents), t-butanol (40 milliequivalents) and water (7.3 milliequivalents) in benzene (3.75 moles/liter of the t-alcohols in benzene) was slowly added and the reaction mixture was stirred for 3 hours and then allowed to stand for 2 days at −15° C., which resulted in the quantitative conversion of the alcohols and water to barium salts. After flash distillation of the amine and benzene, the resulting white solid (11.28 g) was dried at 100° C. under vacuum (20 mm Hg) for one hour to a nitrogen content of not over about 0.01% by weight. A Dry Ice cold trap was disposed between the reactor and the vacuum source to also remove volatiles. Toluene (47.5 g) was added to the salts and the reactor was heated to 70° C. for 2 hours. The total alkalinity of a hydrolyzed aliquot of the clear colorless solution, removed from the excess barium metal, measured 0.148 meq of hydroxide per gram or 2.4 wt. % barium salts, demonstrating total dissolution of the salt. The empirical composition of this product can be represented as:

$$Ba[(t\text{-}BuO)_{1.17}(t\text{-}DecO)_{0.61}(OH)_{0.22}].$$

The relatively high solubility of this barium salt was demonstrated by vacuum distillation (60° C.) of 90 volume % of toluene from a solution of barium salt. A non-saturated solution containing 20 wt % of barium salt in toluene at 25° C. was obtained based on total alkalinity of the concentrated solution. In comparison, maximum solubilities (saturated solution at 25° C. in toluene) of about 1 wt % were found for amine-free (about 0.01 wt. % $N_2$) $Ba[(t\text{-}BuO)_{1.8}(OH)_{0.2}]$ prepared in a similar fashion without the use of t-decanol. The storeageability of these salts is shown in Table 1, below:

TABLE 1

Variation in Solubility at Room Temperature (ca 25° C.), Weight Percent in Toluene, Nitrogen-Free Ba Salts

| Days | Ba(t-BuO). (t-DecO). (OH) | Ba(t-BuO). (OH) |
|---|---|---|
| 0 | 2.4 | .85 |
| 13 | — | .72 |
| 20 | — | .64 |
| 44 | — | .50 |
| 48 | 2.4 | — |
| 61 | — | .46 |
| 69 | — | .45 |
| 79 | 2.17 | — |
| 90 | 2.42 | — |
| 114 | — | .29 |
| 150 | 2.33 | — |

These results show the variation in solubility with time for these barium salts. The superior storage stability of the barium salt containing the t-decoxide radical can be seen from the data in the above table. In addition the t-decoxide containing salt has not appreciably separated out of its solution in toluene even after standing in toluene at 25° C. for 5 months. This, of course, means that the catalyst is generally stable and does not have to be used for polymerization immediately after preparation. A stable, highly soluble catalyst means a catalyst that is easier to use (high solubility) in polymerization and which is more reliable in giving reproducible polymerizations (due to its stability in concentration with time).

EXAMPLE 2

Butadiene-1,3 was solution polymerized in several runs under an argon atmosphere in rotating glass bottles in a polymerization bath following the general procedures shown in U.S. Pat. No. 3,992,561, above. An antioxidant was added to the PBD during work up. The polymerization conditions and the results obtained are shown in Table 2, below:

TABLE 2

| Run No. | Grams BD | Milli Moles n-butyl Lithium | Milli Moles Barium Salt | Ba salt Composition tBuO/t-DecO/OH Mole Ratio |
|---|---|---|---|---|
| 1[a] | 20.0 | .66 | .33 | 91/0/9 |
| 2[b] | 10.9 | .43 | .43 | 91/0/9 |
| 3[b] | 10.8 | .40 | .37 | 59/31/10 |
| 4[b] | 13.5 | .253 | .20 | 59/31/10 |
| 5[b] | 11.4 | .38 | .35 | 48/48/4 |
| 6[b] | 12.2 | .43 | .41 | 67/33/0 |

| Run No. | Mole Ratio $Ba^{2+}/Li^+$ | Polym. Solvent | Polym. Temp. °C. | % Conversion (Hours) |
|---|---|---|---|---|
| 1 | 0.45 | Toluene | 30 | 95(27) |
| 2 | 1.0 | Toluene | 20 | 100(19) |
| 3 | .90 | Toluene | 20 | 100(25) |
| 4 | .80 | Cyclohexane | 25 | 100(24) |
| 5 | .92 | Toluene | 20 | 100(118) |
| 6 | .95 | Cyclohexane | 25 | 100(24) |

| Run No. | Diene Structure % trans | Diene Structure % vinyl | Cryst. Melt Temp. °C. (by DTA[h]) | Intrinsic Viscosity at 25° C. in Toluene, dl/g |
|---|---|---|---|---|
| 1 | 78 | 8 | 29,35 | 4.20 |
| 2 | 80 | 7 | 38 | 6.48 |
| 3 | 82[c] | 7[c] | 12,37,46 | 4.09[d] |
| 4 | 80 | 10 | 10,21,33 | 7.68[e] |
| 5 | 73[f] | 13[f] | 38,48 | 3.74[g] |
| 6 | 79 | 7 | 13,36 | |

[a]Polymerization with amine or nitrogen containing barium salt; see Run 11, columns 12 to 14, of U.S. Pat. No. 3,992,561.
[b]Polymerization with amine-free barium salts of the present invention, e.g., nitrogen content not greater than about 0.01% by weight; see Example 1, above.
[c]Estimated values from infrared spectrum of polymer film.
[d]Based on 66% by weight of polymer in solution; the balance is high molecular weight insoluble polymer - not gel.
[e]Based on 55% by weight of polymer in solution; the balance is high molecular weight insoluble polymer - not gel.
[f]Infrared spectrum of polymer film shows strong absorption for benzyl suggesting extensive chain transfer to toluene. Estimated values from infrared spectrum of polymer film.
[g]Based on 69% polymer in solution; the balance is high molecular weight insoluble polymer - not gel.
[h]Differential Thermal Analysis Table 2 compares the effect of various barium salts on polymerization rate, molecular weight and microstructure. The effective mole ratio for the preparation of 78 or 80% trans-1,4 polybutadiene with an amine containing Ba-Li catalyst complex was 0.45 relative to 1.0 in an amine-free Ba-Li catalyst complex. Higher rates of polymerization and higher molecular weights were obtained with the amine-free system. See Runs 1 and 2, above. The rate effect is further demonstrated in Example 6, below.

By substituting 34 mol % of t-butanol with t-decanol, with or without a small amount of water, in the preparation of the amine(nitrogen)-free barium salt and using it with n-butyl lithium, high molecular weight rubbery polybutadienes having about 80% trans-1,4 placements were obtained in toluene as the polymerization solvent as well as cyclohexane as the polymerization solvent. See Run 3 and 4, above. The intrinsic viscosity of 7.68 dl/g shown in Run 4 based on 55% dissolved polymer is higher than anything reported in the working examples of U.S. Pat. No. 3,992,561. This example demonstrates that polymerizations proceed in the absence of chain transfer to cyclohexane with the above catalyst.

EXAMPLE 3

1275 g. butadiene-1,3 and 225 g. styrene were copolymerized following the above general procedure. The charge to the reactor was by weight 85% of butadiene and 15% of styrene. The final copolymer contained 10 weight % of styrene. Polymerization was conducted under an inert atmosphere in toluene at 13° C. for 43 hours to obtain 89% conversion. The amine-free (not over about 0.01 wt. % nitrogen) barium salt used had the empirical formula:

$$Ba[(t\text{-decoxide})_{0.61}(t\text{-butoxide})_{1.18}(OH)_{0.21}].$$

In the catalyst complex or mixture used in the polymerization the mole ratio of the Ba salt (30 millimole) to n-butyl lithium (45 millimole) was $Ba^{2+}/Li^+ = 0.67$. The copolymer was recovered by coagulation with isopropanol, and the copolymer was vacuum dried at 65°. To the copolymer was added 1% of an antioxidant [2,2'-methylene bis (4-methyl-6-tert-butyl phenol)] and 1.2% of lauric acid. The resulting rubbery butadienestyrene copolymer exhibited the following properties: 76% trans-1,4 and 6% vinyl for the butadiene placements, Tg (glass transition) $-82°$ C. by DTA at a heating rate of 20°/minute, a broad endothermic melt transition near 25° C., a Mooney viscosity (ML-4) at 100° C. of 74 and an intrinsic viscosity of 4.08 dl/g in toluene at 25° C.

EXAMPLE 4

A barium t-butoxide-hydroxide salt having 0.01 wt. % or less of nitrogen was made according to the general method of Example 1, above, but without the t-decanol. It had the empirical formula $Ba[-(\text{+}t\text{-BuO})_{1.8}.\text{+OH})_{0.2}]$. It was used with n-butyllithium to polymerize butadiene-1,3 in toluene at 20° C. The representative charge was 91 g of toluene and 9 g of butadiene-1,3. The amount of n-butyllithium used was 0.55 millimoles (0.13 for titration and 0.42 active). Several runs were made and the results obtained are shown in Table 3, below:

TABLE 3

| Run No. | Mole Ratio $Ba^{2+}/Li^+$ | % Conv. in 24 Hrs. | Intrinsic Viscosity, 25° C. in tol. dl/g(% insolubles) | Diene Structure | |
|---|---|---|---|---|---|
| | | | | % trans | % vinyl |
| 11 | 0 | 98 | 0.58 (1) | 50 | 11 |
| 12 | .24 | 79 | 0.58 (0) | 66 | 11 |
| 13 | .46 | 80 | 3.7 (2) | 73 | 9 |
| 14 | .49 | 95 | 3.52 (8) | 75 | 8 |
| 15 | .81 | 100 | 4.94 (6) | 80 | 8 |
| 16 | .82 | 100 | 7.64 (7) | 82 | 7 |
| 17 | .97 | 100 | 4.91 (12) | 79 | 9 |
| 18 | 1.02 | 100 | 6.48 (24) | 80 | 7 |
| 19 | 1.26 | 47 | 3.92 (10) | 64 | 23 |
| 20 | 1.49 | 42 | 1.61 (3) | 50 | 37 |
| 21 | 3.0 | 20 | 0.82 (0) | 43 | 46 |

TABLE 3-continued (header: Variation in Molecular Structure With Varying Mole Ratio N₂ Free Ba salt/n-butyl Lithium in the Catalyst Complex)

This example shows that operating substantially outside of the delineated mole ratios of $Ba^{2+}/Li^+$ does not provide polybutadienes exhibiting high viscosity and high trans content and does not give high conversions. The insolubles are the high molecular weight portions of the polymers which did not dissolve in the solvent for the viscosity test after 48 hours in the dark with no agitation but are not gels. Moreover, if the polymers are placed in toluene and the mixture is stirred and heated to 50°-60° C. for several hours, total solution results.

EXAMPLE 5

A barium t-decoxide-hydroxide salt (no t-butoxide) made according to Example 1, above, containing not over 0.01% by wt. of nitrogen was used with n-butyl lithium in a mole ratio of $Ba^{2+}/Li^+$ of 0.93 to polymerize butadiene-1,3 in 111 ml of cyclohexane at 25° C. (charge ratio: 13.4 g BD, 0.43 millimole n-BuLi and 0.40 millimole of the Ba salt). After 28 hours only 8.5% conversion of monomer to a sticky gelled polymer was obtained which shows that only t-decanol and water used to make the barium salt does not give the desired results. The polymer also exhibited 65% trans-1,4 content and 15% vinyl content.

EXAMPLE 6

Butadiene-1,3 was polymerized in toluene at 30° C. using n-butyl lithium and a barium salt having the empirical formula $Ba[-(\text{+}t\text{BuO})_{1.8}.\text{+OH})_{0.2}]$ which had been made according to Example 1, above, but which had only been vacuum dried at 50° C. (see Run 11, columns 11 to 14 of U.S. Pat. No. 3,992,561) and accordingly contained an appreciable amount of $N_2$. Table 4A, below, shows the rate of polymerization using optimum polymerization conditions for making high trans BD (mole ratio $Ba^{+2}/Li^+ = 0.5$, 1.5 molar butadiene and $1.5 \times 10^{-3}$ molar BuLi):

TABLE 4A

| Run No. | Time, Hours, Approx. | Percent Conversion |
|---|---|---|
| 31 | 1¾ | 13 |
| 32 | 4 | 34 |
| 33 | 6 | 50 |
| 34 | 9 | 68 |
| 35 | 12 | 80 |

Butadiene-1,3 was likewise polymerized in toluene at 30° C. using n-butyl lithium and a barium salt having the empirical formula $Ba[-(\text{+}t\text{-BuO})_{1.8}.\text{+OH})_{0.2}]$ and made according to Example 1 and which contained 0.01 wt % or less of nitrogen. Table 4B, below, shows the rate of polymerization using optimum polymerization conditions for making high trans BD (mole ratio of $Ba^{2+}/Li^+ = 1.0$, 1.5 molar butadiene and $1.5 \times 10^{-3}$ molar BuLi):

TABLE 4B

| Run No. | Time, Hours, Approx. | Percent Conversion |
|---|---|---|
| 41 | 2 | 60 |
| 42 | 4 | 79 |
| 43 | 6 | 86 |
| 44 | 8 | 95+ |

These results show that faster or higher conversion can be obtained using a barium salt which is nitrogen-free.

EXAMPLE 7

A butadiene-1,3-styrene copolymer was prepared according to the general method of Example 3, above, from n-BuLi and the Ba salt. The barium salt used was prepared according to Example 1, above, and had not over about 0.01 wt. % $N_2$; it had the empirical formula: $Ba[(t-decoxide)_{0.61}(t-butoxide)_{1.18}(OH)_{0.21}]$. The copolymer contained 13.7% by weight of styrene, 76% trans-1,4 units, 8% vinyl units, a Tg of $-85°$ C. by DTA (at a heating rate of 20° C./minute), a broad endothermic melt transition to 25° C., a Mooney viscosity (ML-4) at 100° C. of 63 and an intrinsic viscosity $[\eta]$ of 5.31 dl/g in toluene at 25° C. To the polymer was added 1.0% 2,2'-methylene bis (4-methyl-6-tert butyl phenol) and 1.8% lauric acid.

The tack strength of this copolymer was then compared with natural rubber using the Monsanto "Tel-Tak"[Instrument with a contact load of 32 ounces and at a separation rate of 1 inch/minute after the contact times as specified in Table 5, below:

TABLE 5

| Polymer Description | Contact Time Minutes | Tack Strength PSI |
|---|---|---|
| High trans SBR of this Example | 0.5 | 17 |
| | 3.0 | 22 |
| | 6.0 | 38 |
| High trans SBR of this Example peptized with 1.5 phr of pentachlorothiophenol | 0.5 | 25 |
| | 3.0 | 45 |
| | 6.0 | 47 |
| Natural Rubber (SMR-CV) | 0.5 | 23 |
| | 3.0 | 23 |
| | 6.0 | 27 |

The green strength (stress) of the uncompounded natural rubber at about 690% elongation was about 0.59 MPa. The green strength of the uncompounded unpeptized high trans SBR of this Example at about 650% elongation was about 0.55 MPa.

The high trans SBR rubber of this Example, also, was compared with SBR 1500 (an emulsion cold polymerized copolymer of butadiene and styrene containing about 23.5% styrene). The compounding recipe used and the properties obtained on curing are shown in Table 6, below:

TABLE 6

| Ingredients | High trans SBR of this Example | SBR 1500 |
|---|---|---|
| Rubber | 100 | 100 |
| HAF carbon black | 45 | 45 |
| Oil | 5* | 5** |
| Pentachlorothiophenol (Renacit VII) | 1.5 | — |
| 2,2'-methylene bis (4-methyl-6-tert butyl phenol) | | |
| Mixed diaryl phenylenediamine, ("Wingstay" 100, Goodyear Chem.) | — | 2 |
| ZnO | 5 | 5 |
| Stearic Acid | 3 | 3 |
| Tackifier 775 | 3 | 3 |
| Atlantic Wax | — | 3 |
| N-Oxydiethylene benzothiazole 2-sufenamide ("NOBS" Special, American Cyanamid) | 1.6 | 1.6 |
| Tetramethylthiuram monosulfide | 0.2 | 0.2 |
| "Crystex" (80% sulfur in maineral oil, Stauffer Chem.) | 1.3 | 1.3 |
| *Naphthenic Oil | **"Philrich" No. 5 | |
| Cured minutes/°C. | 32/142 | 45/142 |
| Modulus at 300%, MPa | 4.21 | 6.47 |
| Tensile strength, MPa | 21.41 | 21.94 |
| Elongation, % | 730 | 700 |
| Hardness, Shore A | 59 | 66 |
| Tear Strength, Crescent kN/M | 82.7 | 83.0 |
| Heat build up at 100° C., delta T° C. | 25 | 32 |
| Set %, at 100° C. | 7.6 | 10.2 |
| DeMattia Flex × $10^{-4}$ | 10 | 10 |
| % Crack Growth | 75 | 92 |

We claim:

1. A composition of matter useful in anionic polymerization and comprising a complex of
   A. a compound selected from the group consisting of and having the general formula

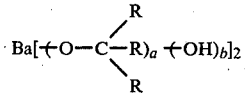

I.

where at least one R is a methyl or cyclohexyl radical and where the remaining Rs are selected from the group consisting of alkyl and cycloalkyl radicals having from 1 to 6 carbon atoms which may be the same or different, and where the mol ratio of a to b is from about 99.5:0.5 to 88:12 and

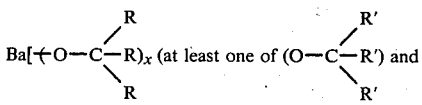

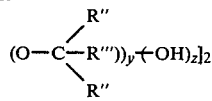

II.

where the Rs are as defined above, where the R's are alkyl radicals of from 2 to 6 carbon atoms which may be the same or different, where the R''s are alkyl radicals of from 1 to 4 carbon atoms which may be same or different and where R''' is a hydrocarbon radical having a molecular weight of from about 250 to 5,000, where the mol ratio of x+y to z is from about 100:0 to 88:12 and where the mol ratio of x to y is from about 1:0.3 to 1:1, said compound A containing not greater than about 0.1% by weight of nitrogen and B. a hydrocarbon lithium compound having from 2 to 200 carbon atoms and from 1 to 6 lithium atoms, the mol ratio of A to B based on barium metal and lithium metal being from about 0.60:1 to 1.1:1.

2. A composition of matter according to claim 1 where the mol ratio of a to b is from about 97.5:2.5 to 90:10 and where the mol ratio of x+y to z is from 100:0 to 90:10, said compound A containing not greater than about 0.01% by weight of nitrogen and where the organo lithium compound is a monolithium alkyl compound containing from 2 to 10 carbon atoms.

3. A composition according to claim 1 where the Rs are methyl radicals, the R's are n-propyl radicals, and the R"s are methyl radicals and the lithium compound is n-butyl lithium.

4. A composition of matter useful in anionic polymerization and comprising a complex of A. a compound having the general formula

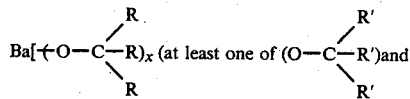 (at least one of 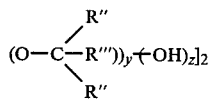and

-continued $$(O-\underset{R''}{\overset{R''}{C}}-R''')_y (OH)_z]_2$$

where at least one R is a methyl or cyclohexyl radical, where the remaining Rs are selected from the group consisting of alkyl and cycloalkyl radicals having from 1 to 6 carbon atoms which may be the same or different, where the R's are alkyl radicals of from 2 to 6 carbon atoms which may be the same or different, where the R"s are alkyl radicals of from 1 to 4 carbon atoms which may be the same or different, where R''' is a hydrocarbon radical having a molecular weight of from about 250 to 5,000, where the mol ratio of x+y to z is from about 100:0 to 88:12 and where the mol ratio of x to y is from about 1:0.3 to 1:1, said compound A containing not greater than about 0.1% by weight of nitrogen and B. a hydrocarbon lithium compound having from 2 to 200 carbon atoms and 1 to 6 lithium atoms, the mol ratio of A to B based on barium metal and lithium metal being from about 0.60:1 to 1.1:1.

5. A composition of matter according to claim 4 where the mol ratio of x+y to z is from about 100:0 to 90:10, said compound A containing not greater than about 0.01% by weight of nitrogen.

6. A composition of matter according to claim 4 where the Rs are methyl radicals, the R's are n-propyl radicals, the R"s are methyl radicals and the lithium compound is n-butyl lithium.

* * * * *